(12) United States Patent
Ibrahim et al.

(10) Patent No.: US 8,211,940 B2
(45) Date of Patent: Jul. 3, 2012

(54) OXALIPLATIN ACTIVE SUBSTANCE WITH A VERY LOW CONTENT OF OXALIC ACID

(75) Inventors: Houssam Ibrahim, Veyrier (CH); Rolland-Yves Mauvernay, Champ du Moulin (CH)

(73) Assignee: Debiopharm S.A., Lausanne (CH)

( * ) Notice: Subject to any disclaimer, the term of this patent is extended or adjusted under 35 U.S.C. 154(b) by 0 days.

(21) Appl. No.: 12/576,383

(22) Filed: Oct. 9, 2009

(65) Prior Publication Data

US 2010/0173988 A1    Jul. 8, 2010

Related U.S. Application Data

(63) Continuation of application No. 10/482,367, filed as application No. PCT/CH02/00358 on Jul. 2, 2002, now abandoned.

(30) Foreign Application Priority Data

Jul. 2, 2001  (WO) .................. PCT/CH01/00414
Oct. 15, 2001 (WO) .................. PCT/CH01/00618

(51) Int. Cl.
*A61K 31/28* (2006.01)
*C07F 15/00* (2006.01)
(52) U.S. Cl. ........................ 514/492; 556/137
(58) Field of Classification Search ............ 556/137; 514/492
See application file for complete search history.

(56) References Cited

U.S. PATENT DOCUMENTS

| | | | |
|---|---|---|---|
| 4,169,846 A | 10/1979 | Kidani et al. | |
| 5,104,896 A | 4/1992 | Nijkerk et al. | |
| 5,290,961 A | 3/1994 | Okamoto et al. | |
| 5,298,642 A | 3/1994 | Tozawa et al. | |
| 5,338,874 A | 8/1994 | Nakanishi et al. | |
| 5,420,319 A | 5/1995 | Okamoto et al. | |
| 5,716,988 A | 2/1998 | Ibrahim et al. | |
| 5,959,133 A | 9/1999 | Ohnishi | |
| 6,396,902 B2 | 5/2002 | Tybinkowski et al. | |
| 6,476,068 B1 | 11/2002 | Lauria et al. | |
| 6,673,805 B2 | 1/2004 | Lauria et al. | |
| 6,866,857 B1 | 3/2005 | Mauvernay | |
| 2003/0109514 A1 | 6/2003 | Lauria et al. | |
| 2003/0109515 A1 | 6/2003 | Lauria et al. | |
| 2008/0319061 A1* | 12/2008 | Kysilka et al. | 514/492 |
| 2010/0174102 A1* | 7/2010 | Kysilka et al. | 556/137 |

FOREIGN PATENT DOCUMENTS

| | | |
|---|---|---|
| EP | 0 625 523 | 11/1994 |
| EP | 0 801 070 | 10/1997 |
| EP | 0 943 331 | 9/1999 |
| WO | WO 96/04904 | 2/1996 |
| WO | WO 99/43355 | 9/1999 |
| WO | WO 00/21527 | 4/2000 |

OTHER PUBLICATIONS

Office Action dated Apr. 15, 2009, from U.S. Appl. No. 10/482,367.
Office Action dated Jun. 25, 2008, from U.S. Appl. No. 10/482,367.
Office Action dated Sep. 4, 2007, from U.S. Appl. No. 10/482,367.
Office Action dated Apr. 10, 2007, from U.S. Appl. No. 10/482,367.
Notice of Allowance dated Jun. 7, 2006, from U.S. Appl. No. 10/482,367.
Office Action dated Feb. 13, 2006, from U.S. Appl. No. 10/482,367.
Office Action dated Jun. 9, 2005, from U.S. Appl. No. 10/482,367.
Office Action dated Oct. 1, 2004, from U.S. Appl. No. 10/482,367.
Dec. 12, 2006, Keppler Declaration.
Sep. 23, 2008, Keppler Declaration.
Letter dated Feb. 2, 2007, from Cabinet Regimbeau to the European Patent Office, providing Third Party Observations for European Patent Application No. 1 404 689.
Translation of Letter dated Feb. 2, 2007, providing Third Party Observations.
Vidal 2000 Dictionary, 76th Edition, Editions Vidal®, Paris, France (2000), pp. 690-692, entry for Eloxatine® 5 mg/ml; and cover, abbreviations, summary, and preface to 76th Edition pages.
Translation of Vidal 2000 Dictionary, 76th Edition, Editions Vidal®, Paris, France (2000), pp. 690-692, entry for Eloxatine® 5 mg/ml and cover page.
Request for Cancellation in corresponding German Utility Model No. 202 21 678, dated Oct. 25, 2007.
English Translation of Request for Cancellation in corresponding German Utility Model No. 202 21 678, dated Oct. 25, 2007.
Request for annulment of German Utility Model No. 202 21 678, dated Aug. 7, 2007.
English Translation of Request for annulment of German Utility Model No. 202 21 678, dated Aug. 7, 2007.
Judgment 3 Ni 15/01 (EU), (2002).
English Translation of Judgment 3 Ni 15/01 (EU), (2002).
Judgment 3 Ni 9/02 (EU), (2003).
English Translation of Judgment 3 Ni 9/02 (EU), (2003).
2002 Annual Report of the Federal Patent Court, pp. 18-19.
English Translation of 2002 Annual Report of the Federal Patent Court, pp. 18-19.
Submission from Debiopharm to European Patent Office dated Apr. 10, 2007.

(Continued)

*Primary Examiner* — Porfirio Nazario Gonzalez
(74) *Attorney, Agent, or Firm* — R. Brian McCaslin

(57) ABSTRACT

The present invention relates to an oxaliplatin active substance for a pharmaceutical composition, wherein its weight content in oxalic acid is not more than 0.08%, and to a process of preparing the active substance.

6 Claims, No Drawings

OTHER PUBLICATIONS

Letter dated Jul. 5, 2007, from Cabinet Regimbeau to the European Patent Office, providing Third Party Observations for European Patent Application No. 1 404 689.
English translation of Letter dated Jul. 5, 2007, providing Third Party Observations.
Enclosure to Third Party Observations, EPO Appeal Decision T 0150/82, dated Feb. 7, 1984.
English translation of enclosure to Third Party Observations, EPO Appeal Decision T 0150/82, dated Feb. 7, 1984.
European Patent Office Examination Report in corresponding European Patent Application No. 1 404 689, dated Apr. 13, 2006.
European Patent Office Examination Report in corresponding European Patent Application No. 1 404 689, dated Sep. 23, 2005.
Pharmeuropa, Jul. 2001, 585-588, 13(3).
International Search Report in PCT/CH02/00358 (which is the International Application for European App. No. 02 734 974.5) dated Nov. 7, 2002.
International Preliminary Examination Report in PCT/CH02/00358 (which is the International Application for European App. No. 02 734 974.5) dated Oct. 8, 2003.
Alberts, S. R., et al. "Gemcitabine and oxaliplatin for patients with advanced or metastatic pancreatic cancer: a North Central Cancer Treatment Group (NCCTG) phase I study," *Annals of Oncology*, 13: 553-557 (2002).
Alberts, S.R. "Intrahepatic Therapy for Resected Hepatic Metastases from Colorectal Carcinoma," *Oncology*, 14(12: Suppl. 11): 48-51 (2000).
Berlin, J. "Second-Line Therapy in Colorectal Cancer," *Oncology*, 14(12: Suppl. 11): 21-26 (2000).
Goldberg, R. "Oxaliplatin in Colorectal Cancer: Current Studies," *Oncology*, 14(12: Suppl. 11): 42-47 (2000).
Haller, D.G. "Safety of Oxaliplatin in the Treatment of Colorectal Cancer," *Oncology*, 14(12: Suppl. 11): 15-20 (2000).
Kemeny, N., et al. "Phase I study of weekly oxaliplatin plus irinotecan in previously treated patients with metastatic colorectal cancer," *Annals of Oncology*, 13: 1490-1496 (2002).
Kidani, Y., et al. "Preparative development of antitumor 1,2-cyclohexanediamine platinum complexes," *Trends in Inorganic Chemistry*, 1(1): 107-125 (1990).
Kidani, Y., et al. "Antitumor Activity of Platinum(II) complexes of 1,2-Diaminocyclohexane Isomers," *Gann*, 71: 637-643 (1980).
Khushalani, N. I., et al. "Oxaliplatin in Combination With Protracted-Infusion Fluorouracil and Radiation: Report of a Clinical Trial for Patients With Esophageal Cancer," *J. Clin. Oncology*, 20: 2844-2850 (2002).
Larocca, R.V., et al. "Compassionate-use Oxaliplatin with Bolus 5-Fluorouracil/Leucovorin in Heavily Pretreated Patients with Advanced Colorectal Cancer," *Southern Med. J.*, 97(9): 831-835 (2004).
Liu, J., et al. "Dosing sequence-dependent pharmacokinetic interaction of oxaliplatin with paclitaxel in the rat," *Cancer. Chemother. Pharmacol.*, 50: 445-453 (2002).
Lorusso, P.M. "Oxaliplatin in Tumors Other Than Colorectal Cancer," *Oncology*, 14(12: Suppl. 11): 33-37 (2000).
Mani, S., et al. "Novel Combinations with Oxaliplatin," *Oncology*, 14(12: Suppl. 11): 52-58 (2000).
Mitchell, E.P. "Oxaliplatin with 5-FU or as a Single Agent in Advanced/Metastatic Colorectal Cancer," *Oncology*, 14(12: Suppl. 11): 30-32 (2000).
Ramanathan, R.K., et al. "Safety and Toxicity Analysis of Oxaliplatin Combined with 5-Fluorouracil or as a Single Agent in Patients With Previously Treated Advanced Colorectal Cancer," *J. Clin. Oncol.*, 21(13): 2904-2911 (2003).
Rothenberg, M.L. "Efficacy of Oxaliplatin in the Treatment of Colorectal Cancer," *Oncology*, 14(12: Suppl. 11): 9-14 (2000).
Ryan, D.P. "Rectal Cancer: Integrating Oxaliplatin Into Chemoradiation Studies," *Oncology*, 14(12: Suppl. 11): 38-41 (2000).
Shord, S. S. et al. "Oxaliplatin Biotransformation and Pharmacokinetics: A Pilot Study to Determine the Possible Relationship to Neurotoxicity," *Anticancer Research*, 22: 2301-2310 (2002).
Teicher, B. A., et al. "Treatment Regimens Including the Multitargeted Antifolate LY231514 in Human Tumor Xenografts," *Clin. Cancer Res.*, 6: 1016-1023 (2000).
Wolmark, N., et al. "National Surgical Adjuvant Breast and Bowel Project Trials in Colon Cancer," *Semin. Oncol.* 1(1): 9-13 (2001).
Certificate of Analysis of Oxaliplatin, 1987 (Exhibit A).
Certificate of Analysis, Apr. 1987 (Exhibit B).
Certificate of Analysis of Oxaliplatin Batch 91-011 (Exhibit C), (1992).
21 C.F.R. § 312.34 (Exhibit E), (1998).
Statement by Robert J. Temple Before The H. Comm. on Government Reform, 107th Cong. 4-6 (2001) available at http://www.fda.gov/ola/2001/compassionateuse0620.html). (Exhibit F).
Declaration of Bernard Keppler (Exhibit G), (2006).
Report of Professor Thomas Ward regarding Comparative Example 2 (Exhibit H), (2006).
European Pharmacopoeia entry for oxaliplatin (Exhibit I), (2001).
Redacted Sanofi, Dakota Pharm., Debiopharm, Contrat de Sous-License, Nov. 9, 1994 (Exhibit J).
English Translation of Redacted Sanofi, Dakota Pharm., Debiopharm, Contrat de Sous-License, Nov. 9, 1994 (Exhibit J).
Redacted Sanofi, Dakota Pharm., Debiopharm, Contrat de Sous-License, Mar. 29, 1996 (Exhibit K).
English Translation of Redacted Sanofi, Dakota Pharm., Debiopharm, Contrat de Sous-License, Mar. 29, 1996 (Exhibit K).
Sanofi, Debiopharm Contrat de Fourniture, Jul. 25, 1996 (redacted)(Exhibit L).
English Translation of Redacted Sanofi, Debiopharm Contrat de Fourniture, Jul. 25, 1996 (Exhibit L).
Development, Manufacturing, and Supply Contract between Debiopharm and Ben Venue Laboratories, 1994 (redacted) (Exhibit M).
*Tone Bros. v. Sysco Corp.*, 28 F.3d 1192 (Fed. Cir. 1994).
*Kilbey v. Thiele*, 199 U.S.P.Q. 290 (B.P.A.I. 1978).
*Graham v. John Deere Co. of Kansas City*, 383 U.S. 1 (1966).
*In re Wood*, 599 F.2d 1032 (C.C.P.A. 1979).
*In re Fritch*, 972 F.2d 1260 (Fed. Cir. 1992).
1 Samuel Williston, *A Treatise on the Law of Contracts* § 5.2 (1990).
*Gandy v. Main Belting Co.*, 143 U.S. 587 (1892).
*Group One, Ltd. v. Hallmark Cards, Inc.*, 254 F.3d 1041 (Fed. Cir. 2001).
*In re Caveney*, 761 F.2d 671 (Fed. Cir. 1985).
*Pfaff v. Wells Elecs., Inc.*, 525 U.S. 55 (1998).
*Allen Eng'g Corp. v. Bartell Indus., Inc.*, 299 F.3d 1336 (Fed. Cir. 2002).
*Monon Corp. v. Stoughton Trailers, Inc.*, 239 F.3d 1253 (Fed. Cir. 2001).
*Enzo Biochem, Inc. v. GenProbe, Inc.*, 424 F.3d 1276 (Fed. Cir. 2005).
*Special Devices, Inc. v. OEA, Inc.*, 270 F.3d 1353 (Fed. Cir. 2001).
*Brasseler U.S.A. I., L.P. v. Stryker Sales Corp.*, 182 F.3d 888 (Fed. Cir. 1999).
*EZ Dock, Inc. v. Schafer Sys., Inc.*, 276 F.3d 1347 (Fed. Cir. 2002).
*In re Kollar*, 286 F.3d 1326 (Fed. Cir. 2002).
*Smith v. Sprague*, 123 U.S. 249 (1887).
21 C.F.R. § 312.7, (2008).
21 C.F.R. §§ 312.50, 56, and 59-61, (2008).
*TP Labs., Inc. v. Professional Positioners, Inc.*, 724 F.2d 965 (Fed. Cir. 1996).
*SmithKline Beecham Corp. v. Apotex, Inc.*, 286 F.Supp.2d 925 (N.D. III. 2001), vacated, *Smithkline Beecham Corp. v. Apotex Corp.*, 403 F.3d 1328 (Fed. Cir. 2005).
*SmithKline Beecham Corp. v. Apotex, Inc.*, 365 F.3d 1306 (Fed. Cir. 2004), vacated, *Smithkline Beecham Corp. v. Apotex Corp.*, 403 F.3d 1328 (Fed. Cir. 2005).
*SmithKline Beecham Corp. v. Apotex, Inc.*, 403 F.3d 1328 (Fed. Cir. 2005).
*Janssen Pharm. N.V. v. Eon Labs Manf., Inc.*, 374 F.Supp.2d 263 (E.D. N.Y. 2004).
*Janssen Pharm. N.V. v. Eon Labs Manf., Inc.*, 134 Fed. Appx. 425 (Fed. Cir. 2005)(nonprecedential).
*Eli Lilly & Co. v. Zenith Goldline Pharm., Inc.*, Nos. 05-1396, 05-1429, 05-1430 (Fed. Cir., Dec. 26, 2006).

*Elan Corp.* v. *Andrx Pharms.•* 366 F.3d 1336 (Fed. Cir. 2004).
*Elizabeth* v. *Pavement Co.*, 97 U.S. 126 (1877).
*Honeywell Int'l., Inc.* v. *Universal Avionics Syst., Corp.*, 488 F.3d 982 (Fed. Cir. 2007).
*Lacks Indus., Inc.* v. *McKechnie Vehicle* Components *USA, Inc.*, 322 F.3d 1335 (Fed. Cir. 2003).
*Michael Halebian N.J., Inc.* v. *Rappe Rubber Corp.*, 718 F. Supp. 348 (D. N.J. 1989).
*Zacharin* v. *United States*, 213 F.3d 1366 (Fed. Cir. 2000).
Ebewe Pharma GES.M.BH NFG. KG's Supplemental Memorandum in Support of Sandoz, Inc:S Motion for Summary Judgment of Invalidity of the '988 Patent Claims Under 35 U.S.C. § 102 dated Nov. 25, 2008.
Ebewe Pharma GES.M.B.H. NFG.KG's Objection and Supplemental Response to Plaintiff's Counterstatement of Undisputed Facts dated Jan. 12, 2009 (redacted).
Ebewe Pharma GES.M.B.H. NFG.KG's Supplemental Reply Memorandum in Support of Sandoz, Inc.'s Motion for Summary Judgment of Invalidity of the '988 Patent Claims Under 35 U.S.C. § 102 dated Jan. 12, 2009.
Defendant Sandoz, Inc.'s Reply Memorandum of Law in Support of Its Motion for Summary Judgment of Invalidity of the '988 Patent Claims Under 35 U.S.C. § 102 dated Jan. 12, 2009 (redacted).
Sandoz Responses to Sanofi Statement of Facts dated Jan. 12, 2009 (excerpted and redacted, 6 pages).
Plaintiffs' Memorandum of Law in Opposition to Defendants' Motions for Summary Judgment of Invalidity of the '988 Patent Claims Under 35 U.S.C. § 102 dated Dec. 23, 2008 (redacted).
Plaintiffs' Counterstatement of Undisputed Facts in Response to Defendants' Motions for Summary Judgment of Invalidity of the '988 Patent Under 35 U.S.C. § 102 dated Dec. 23, 2008 (redacted).
Plaintiffs' Responses to Defendants' Statements of Material Facts dated Dec. 23, 2008 (redacted).
Declaration of Robert S. Langer, Sc.D. from Opposition to Sandoz' invalidity of the '988 patent dated Dec. 23, 2008 (redacted).
Declaration of Brendan O'Malley, Esq. from Opposition to Sandoz' invalidity of the '988 patent dated Dec. 23, 2008 (redacted).
*Abbott Labs* v. *Geneva Pharms., Inc.*, 182 F.3d 1315 (Fed. Cir. 1999).
*Anderson* v. *Liberty Lobby, Inc.*, 477 U.S. 242 (1986).
*Atlanta Attachment Co.* v. *Leggett & Platt, Inc..*, 516 F,3d 1361 (Fed. Cir. 2008).
Ben Venue Laboratories and Debiopharm Jan. 13, 1994, Contract (further un-redacted).
Boughattas, N. A., et al., "Circadian Rhythm in Toxicities and Tissue Uptake of 1,2-Diammino-cyclohexane(trans-1 )oxalatoplatinum(II) in Mice," *Cancer Research* (1989) 49:3362-3368.
*Cargill, Inc.* V. *Canbra Foods, Ltd.*, 476 F.3d 1359 (Fed. Cir. 2007).
*Continental Plastic Containers* V.*Owens Brockway Plastic Prods., Inc.*, 141 F.3d 1073 (Fed. Cir. 1998).
*Electromotive Div. of Gen'l Motors Corp.* V *Transportation Sys. Div. of General Elec. Co.*, 417 F.3d 1203 (Fed. Cir. 2005).
E-mail dated Sep. 16, 2008, from Tom Irving forwarding Pre-interview paper (1 page).
E-mail correspondence dated Sep. 23 and 25, 2008, between Tom Irving regarding Interview Summary (8 pages).
English Translation of Mianzhu, X., et al. "Chapter 9: Injections" in *Textbook* (or *Medical & Pharmaceutical colleges and Universities*, People's Health Press (1988), pp. 175-186.
English Translation of Notification of annulment of German Utility Model No. 202 21 678, dated Oct. 2, 2008.
English Translation of Shaoping, Pu, et al., "Synthesis and Characterization of Oxaliplatin," *Precious Metals* (2000) 21(1):26-27.
English Translation of Shenghai, Y. et al., "Advances in pharmacological and clinical studies on oxaliplatin, a new anti-cancer drug" *Foreign Medical Science, Oncology* (1992) 19(5): 271-273.
*Impax Labs., Inc*, v *Aventis Pharm, Inc.*, 545 F.3d 1312, 1315 (Fed. Cir. 2008).

*In re Cygnus Telecomm Tech., LLC; Patent Litig.*, 536 F.3d 1343 (Fed. Cir. 2008).
*In re Omeprazole Patent Litigation*. 536 F.3d 1361 (Fed. Cir. 2008).
*Invitrogen Corp.* v. *Biocrest Mfg. L.P.*, 424 F.3d 1374 (Fed. Cir. 2005).
Khokhar, A. R., et al., "Synthesis and Antitumor Activity of 1.2-Diarninocyclohexane Platinum(IV) Complexes," *Journal of Inorganic Biochemistry* (1994) 54:39-47.
Kidani, Y. "Oxaliplatin," *Drugs of the Future* (1989 )14(6):529-532.
Kidani, Y. et al. "Antitumor Activity of 1,2-Diaminocyclohexane-Platinum Complexes against Sarcoma-180 Ascites Form" *J. Med. Chem.* (1978) 21(12):1315-1318.
Mathe, G. at al., "Oxalato-platinum or 1-OHP, a third-generation platinum complex: an experimental and clinical appraisal and preliminary comparison with cis-platinum and carboplatinum," *Biomed. & Pharmacother.* (1989) 43:237-250.
*MDS Assocs., Ltd. P'ship* v. *U.S.*, 37 Fed. Cl. 611 (1997), *aff'd*, 135 F.3d 778 (Fed. Cir.1998).
Mianzhu, x., et al. "Chapter 9: Injections" in *Textbook for Medical & Pharmaceutical colleges and Universities*, People's Health Press (1988), pp. 175-186.
*Minton* v. *National Assoc. .of Securities Dealers, Inc.*, 336 F.3d 1373 (Fed. Cir. 2003).
Misset, J. L., et al., "Oxalatoplatinum (1-OHP): Experimental and Clinical Studies," *Platinum and Other Metal Coordination Compounds in Cancer Chemotherapy (1991)* Howell, S.B., ed., Planum Press pp. 369-375.
*Mosaid Tech Inc.* v. *Samsung Elec. Co., Ltd.*, 362 F. Supp. 2d 526 (D.N.J. 2005).
*New Railhead Mfg. LLC.* v. *Vermeer Mfg. Co.*, 298 F.3d 1290 (Fed. Cir. 2002).
Notification of annulment of German Utility Model No. 202 21 678, dated Oct. 2, 2008.
Pre-interview Paper to the Examiner dated Sep. 15, 2008.
Professor Keppler's September 231 2008, Declaration.
Reynolds, J. E. F., ed *Martindale the Extra Pharmacopoeia* (1993), pp. 463 and 496.
Sandoz Motion for Summary Judgment in Civil Action No. 3:07-cv-02762-JAP-JJH (redacted), (2000).
*Scaltech, Inc.* V. *Retec/Tetra, LLC*, 269 F.3d 1321 (Fed. Cir. 2001).
Shaoping, Pu et al., Synthesis and Characterization of Oxaliplatin,• *Precious Metals* (2000) 21(1):26-27.
Shenghai, Y. et al, Advances in pharmacological and clinical studies on oxaliplatin, a new anti-cancer drug, *Foreign Medical Science, Oncology* (1992) 19(5): 271-273.
*STX, LLC* v. *Brine, Inc.*, 211 F.3d 588 (Fed. Cir. 2000).
Trissel, L. A. *Handbook on Injectable Drugs*, 8th Ed. (1994), pp. 149-150 and 261-262.
Request for annulment of German Utility Model No. 202 21 678, dated Feb. 27, 2008.
English Translation of Request for annulment of German Utility Model No. 202 21 678, dated Feb. 27, 2008.
Grolleau et al, "A Possible Explanation for a Neurotoxic Effect of the Anticancer Agent Oxaliplatin on Neuronal Voltage-Gated Sodium Channels", The American Physiological Society. 2001, pp. 2293-2297.
European Pharmacopia, 1997 Edition, pp. 283-286.
Chemical Abstracts Service, Zhu et al, "Studies on a sustained-release procainamide hydrochloride tablet—an oral osmotic pump", Yaoxue Xeubao; 1988,23(11), pp. 850-856.
Chemical Abstracts Service, Bradbrook et al, "Comparison of pharmacokinetic profiles of single and multiple doses of a slow release Oros oxprenolol delivery system in young normotensive and elderly hypertensive subjects", Br. J. Clin. Pharmacol., 1986, 21 (4), pp. 371-376.

\* cited by examiner

OXALIPLATIN ACTIVE SUBSTANCE WITH A VERY LOW CONTENT OF OXALIC ACID

This is a continuation of application Ser. No. 10/482,367, filed Dec. 30, 2003 now abandoned, which was a national stage application under 35 U.S.C. §371 of International Application No. PCT/CH02/00358, filed on Jul. 2, 2002, which claims priority to PCT/CH01/00618, filed Oct. 15, 2001 and PCT/CH01/00414, filed Jul. 2, 2001. Applicants claim priority to PCT/CH01/00618, filed Oct. 15, 2001, but affirmatively disclaim priority to PCT/CH01/00414, filed Jul. 2, 2001.

The present invention relates to an oxaliplatin active substance for a pharmaceutical composition, which active substance has a very low content of oxalic acid, to a process for preparing said active substance, to the use thereof for preparing a pharmaceutical composition, in particular by dissolving thereof in an aqueous medium, and to pharmaceutical compositions thereby obtained, notably in the form of a lyophilisate formulation, a liquid formulation or a sustained release formulation for parenteral or oral administration.

Oxaliplatin (INN) or cis-oxalato(trans-l-1,2-diaminocyclohexane)-platinum (II) (CAS RN: 61825-94-3), is a diamine cyclohexane platinum derivative which is active in several solid tumour types such as colorectal cancers.

The molecular structure of that compound and its pharmaceutical properties were first disclosed by Kidani et al. in J. Med. Chem., 1978, 21, 1315, and in U.S. Pat. No. 4,169,846. The proposed general recipe to prepare that compound leads to the compound with such a low yield that it could not be envisaged to be performed on an industrial scale. Improved methods for synthesizing oxaliplatin were then disclosed in the patent literature (see e.g. U.S. Pat. Nos. 5,290,961, 5,298, 642 and 5,338,874, European Patent Publications Nos. 625523 and 801070).

All these published methods of synthesis of oxaliplatin include as last step the substitution in an aqueous solution of the two aquo ligands on Pt (II) by dicarboxylate coming from oxalic acid or an oxalate salt, that step being conducted in a slight excess of oxalic acid or oxalate salt. In spite of a disclosed subsequent purification step there is some residual oxalic acid in the purified oxaliplatin.

The presence of some residual oxalic acid in the oxaliplatin active substance obtained by such methods has however never been recognized as representing a problem although its relative toxicity was well documented in the literature.

For example U.S. Pat. No. 5,290,961 and European Patent Publication No. 801070 describe processes of preparing oxaliplatin that is substantially free of impurities such as by-products containing silver ions, halogen atoms or a Pt (IV) complexes. Oxalic acid is not mentioned as an impurity.

PCT Patent Publication No. 99/43355 discloses the stabilizing effect of adding oxalic acid as a buffering agent to oxaliplatin aqueous pharmaceutical formulations.

Neurotoxicity is a severe dose-limiting side effect of oxaliplatin. F. Grolleau et al., 2001, "A possible explanation of a neurotoxic effect of anticancer agent oxaliplatin on neuronal voltage-gated sodium channels," The American Physiological Society, 2293-2297, have shown in vitro on neuronal voltage-gated sodium channels that oxalate ions, which represent a major metabolite of oxaliplatin biotransformation, may be responsible for the neurotoxicity of that compound.

The problem addressed by the invention is to find an oxaliplatin active substance and a process for preparing that active substance, wherein a pharmaceutical composition containing that active substance has a reduced toxicity.

The above problem is solved by the invention as defined in the appended set of claims.

The invention thus relates to an oxaliplatin active substance for a pharmaceutical composition, wherein its weight content in oxalic acid is not more than 0.08%, in particular not more than 0.05%, most preferably less than 0.02%.

That oxaliplatin active substance may be prepared by a process close to that described in U.S. Pat. No. 5,290,961, which further includes compared to either of those processes, washing 2 to 5 times with water having a pH 4.5-7.0 the oxaliplatin crystals separated by filtration after reaction with alkali metal salt of oxalic acid, and washing 2 to 5 times the recrystallised crystals with water having a pH 4.5-7.0, the amount of water being used in those washings being sufficient for attaining the desired weight content in oxalic acid.

The invention thus also concerns a process for preparing the above defined active substance comprising the following steps (a) reacting in aqueous solution potassium tetrachloroplatinate $K_2PtCl_4$ with trans-l-1,2-cyclohexanediamine, such as to obtain dichloro(trans-l-1,2-cyclohexanediamine)-platinum (II);

(b) adding 1.6 equivalents in respect to the compound obtained in (a) of silver nitrate, such as to obtain diaquo(trans-l-1,2-cyclohexanediamine)-platinum (II);

(c) optionally adding to the obtained solution a catalytic amount of potassium iodide or sodium iodide, stirring and adding active carbon under stirring;

(d) filtering and adding to the obtained filtrate alkali metal salt of oxalic acid such as lithium, sodium, potassium salt, preferably potassium salt, separating the oxaliplatin crystals formed by filtration and washing up to 5 times those crystals with water having a pH 4.5-7.0; and (e) purifying oxaliplatin by recrystallisation wherein the crystals are collected on a filter and washed up to 5 times with water having a pH 4.5-7.0, wherein the amount of water used in washing during steps (d) and (e) is sufficient to attain the desired weight content in oxalic acid.

The person skilled in the art will readily select the appropriate volume of water having a pH 4.5-7.0 used at each washing in step (d) or step (e) in view of the desired content of oxalic acid in the oxaliplatin active substance and the acceptable yield in oxaliplatin. That volume is generally not more than 10 ml per gram of active substance. The respective content of residual oxalic acid in each crop is quantified by an appropriate high performance liquid chromatography method.

The above-defined oxaliplatin active substance may be used for preparing a pharmaceutical composition useful in cancer treatment which presents a reduced toxicity compared to pharmaceutical compositions prepared using an oxaliplatin active substance of the prior art.

Generally the preparation of such a pharmaceutical composition includes the step of dissolving the active substance in an aqueous medium.

The invention is thus related to the use of the above oxaliplatin active substance for preparing a pharmaceutical composition, to a process for preparing the same comprising the step of dissolving the active substance in an aqueous medium, to a pharmaceutical composition obtainable by that process and to a new pharmaceutical composition which contains that active substance, along with pharmaceutically acceptable excipients. Due to the complex physicochemical interactions that take place in the aqueous medium, which may include dissociation to a low degree of oxaliplatin into oxalic acid and diaquo(trans-l-1,2-cyclohexanediamine)-platinum (II), the oxalic acid weight content may be higher when the oxaliplatin active substance is in aqueous medium than when it is in anhydrous state.

The pharmaceutical composition may be a lyophilisate pharmaceutical formulation for parenteral or oral administration. Such a formulation is conveniently obtained by completely dissolving, at a temperature about 40° C. and under stirring, oxaliplatin in a solution of an excipient such as lactose monohydrate in sterile water, then filtering once for clarification and one or more times for sterilisation, aliquoting the filtrate solution into vials and performing freeze-drying using cycles of freezing, primary drying (sublimation) and secondary drying according to techniques well known in the art.

The weight content of oxalic acid in the lyophilisate pharmaceutical formulation is preferably not more than 0.60%, more preferably not more than 0.30%, most preferably not more than 0.20%.

The pharmaceutical composition may also be a liquid pharmaceutical formulation for parenteral administration. Such a formulation is generally obtained by completely dissolving oxaliplatin in sterile water, at a temperature about 40° C. and under stirring, then filtering once for clarification and one or more times for sterilisation, as described in PCT Patent Publication No. 96/04904.

The weight content of oxalic acid in the liquid pharmaceutical formulation is preferably not more than 0.60%, more preferably not more than 0.30%, in particular not more than 0.20%.

The pharmaceutical composition may also be a sustained release formulation including biodegradable polymeric material, notably in the form of microparticles, microspheres, microgranules, implants or gels. Preparation of such an oxaliplatin sustained release formulation may be performed according to techniques well known in the art, with the limitation that all steps must be performed at a pH where the oxaliplatin active substance is stable, preferably between 4.5 and 7.0. An example of an appropriate method for preparing a sustained release formulation of microspheres is the process for preparing oxaliplatin encapsulating poly(D,L-lactide-co-glycolide)/poly(D,L-lactide) (PLGA/PLA) microspheres described in PCT Patent Publication No. 02/28386.

The examples which follow will serve to better describe the invention, but are in no way to be considered as limitative.

EXAMPLE 1

Preparation of an Oxaliplatin Active Substance with a Very Low Content of Oxalic Acid by Applying Modifications of the Method Described in U.S. Pat. No. 5,290,961

562.5 g of potassium chloroplatinate and 154.8 g of trans l-1,2-cyclohexanediamine are dissolved and mixed in 3.5 litres of water to obtain cake-like cisdichloro(trans-l-1,2-cyclohexanediamine)-platinum (II) without recrystallisation. The latter compound is suspended in 5.7 litres of water to which is added a solution which is prepared by dissolving 386.4 g of silver nitrate in 2.8 litres of water. After this solution is stirred in the dark at room temperature for three days, most of the precipitate of silver chloride is removed by filtration. After the filtrate is concentrated under reduced pressure, a solution consisting of 45 ml of water and 3.85 g of potassium iodide dissolved therein is added followed by one hour stirring, and then active carbon is added. Silver iodido and iodine compounds then formed and the active carbon are completely removed by filtration. To the remaining filtrate is added 299.4 g of potassium oxalate monohydrate which is allowed to stand for two hours to obtain crude crystals of desired cis-oxalate (trans l-1,2-cyclohexanediamine)-platinum (II) which are collected by filtration and washed twice with 200 ml of sterile water of pH 5.9. Then, 65 g of this crude crystal is dissolved under heating in 2.7 litres of water, filtered and cooled to room temperature. The platinum crystals precipitated are collected by filtration and washed four times with 150 ml of water of pH 6.5. The crystals obtained are dried.

The weight content of oxalic acid in the oxaliplatin active substance is determined using a hereafter briefly described specific ion-pair reverse phase HPLC test which has a detection limit of 0.02 w/w % for oxalic acid.

The test solution consists of oxaliplatin dissolved using sonication at the concentration of 2 mg/ml in water. The specific ion-pair reverse phase HPLC test is conducted at pH 6.0±0.05 and a temperature of 40° C. on a glass column of diameter 4.6 mm and length 25 cm containing a base-deactivated octadecylsilyl silica gel for chromatography, with a mobile phase consisting of 20 volumes of acetonitrile and 80 ml of a solution prepared by adding 1.36 g potassium dihydrogen phosphate to 10 ml 0.4 M tetrabutylammonium hydroxide and adjusting the pH to 6.0±0.05 with phosphoric acid, a flow rate of 2 ml/minute and UV detection at 205 nm.

EXAMPLE 2

Comparative Example

Preparation of an Oxaliplatin Active Substance According to One of the Methods Described in EP Patent Application No. 625523

Potassium tetrachloroplatinate (3.40 g) was stirred at room temperature with trans-l-1,2-cyclohexanediamine (0.94 g) in aqueous solution (80 ml). The clear orange solution present at the onset of the reaction rapidly turned yellow with a precipitate beginning to form after 30 minutes. The reaction mixture was stirred overnight (14 hours) and filtered. The yellow precipitate was washed with water and dried under vacuum. The crude obtained product (2.98 g) was recrystallised from 6 litres of boiling 0.1N HCl. Upon cooling to room temperature, crystals of dichloro-(trans-l-1,2-cyclohexanediamine)-platinum (II) (2.33 g) were collected by filtration. In parallel, an aqueous solution of oxalic acid (1.29 g, in 10 ml of water) was added dropwise to an aqueous suspension of silver carbonate (2.64 g, in 10 ml of water). Upon stirring 15 minutes at room temperature, carbon dioxide evolution ceased, suggesting a quantitative formation of silver oxalate. The off-white precipitate was collected by filtration. The filtrate was washed abundantly with water and dried under vacuum. To an aqueous suspension of dichloro (trans-l-1,2-cyclohexanediamine)-platinum (II) (1.5 g, in 120 ml of water) as obtained above, silver oxalate (1.199 g) was added as a solid and stirred for 4 hours at room temperature in the dark. With time, the yellow suspension became paler. The precipitate silver chloride was removed by filtration. The resulting clear solution was concentrated to 15 ml to yield a yellow precipitate. After standing at room temperature for 1 hour, the pale yellow precipitate was collected by filtration, yielding to cis-oxalato (trans-l-1,2-cyclohexane-diamine)-platinum (II).

A sample has been analyzed by applying the above-described HPLC method and oxalic acid was detected, corresponding to a weight content of oxalic acid of w/w 0.19% for the oxaliplatin active substance.

EXAMPLE 3

Preparation of a Pharmaceutical Composition in the Form of a Liquid Formulation for Parenteral Administration Using the Oxaliplatin Active Substance of the Invention In a glass or inox container equipped with a thermostat, about 80% of the desired sterile water are introduced and the temperature is brought under stirring (800-1200 rpm) to a temperature of 40±5° C.

The amount of oxaliplatin active substance (as can be obtained in Example 1) necessary to obtain a final concentration for example of 5 mg/ml is separately weighed, then added in preheated sterile water to the sterile water in the glass or inox container. The weighing container is rinsed three times with sterile water, the rinsing solution being added to the above mixture. The latter is stirred at the above temperature during 30 to 60 minutes, until complete dissolution of oxaliplatin. Optionally the water is bubbled with nitrogen to lower its oxygen content.

The volume or weight of the solution is adjusted to its desired value by adding sterile water. The solution is stirred at 40±5° C. during about 10 minutes then cooled to 30° C. under stirring. Samples of the solution are then collected for the usual control tests. The solution is then subjected to aseptic filtration on a 0.2 μm membrane or alternatively autoclaving under conditions close to those described in European Pharmacopia 1997 Edition page 283-284 (minimum of 121° C. for 15 minutes). The solution is kept at 15-30° C. before being conditioned.

The oxaliplatin solution for example at 5 mg/ml is then aseptically and preferably under nitrogen atmosphere conditioned in 5 ml cylindrical vials (volume of added solution about 4 ml corresponding to 20 mg available oxaliplatin), 15 ml cylindrical vials (volume of added solution about 10 ml corresponding to 50 mg available oxaliplatin), and 25 ml cylindrical vials (volume of added solution about 20 ml corresponding to 100 mg available oxaliplatin).

Those vials are kept during 12 months partly in an incubator at 25° C. and a relative humidity of 60% and partly in an incubator at 40° C. and a relative humidity of 75%.

EXAMPLE 4

Preparation of a Pharmaceutical Composition in the Form of a Lyophilisate for Parenteral Administration Using the Oxaliplatin Active Substance of the Invention In a glass or inox container equipped with a thermostat, about 80% of the desired sterile water are introduced and the temperature is brought under stirring (800-1200 rpm) to a temperature of 38±5° C. Lactose monohydrate is added under stirring until a final concentration of 45 mg/ml.

The amount of oxaliplatin active substance (as can be obtained in Example 1) necessary to obtain a final-concentration for example of 5 mg/ml is separately weighed, then added in preheated sterile water to the sterile water in the glass or inox container. The weighing container is rinsed three times with sterile water, the rinsing solution being added to the above mixture. The latter is stirred at the above temperature during 30 to 60 minutes, until complete dissolution of oxaliplatin. Optionally the water is bubbled with nitrogen to lower its oxygen content.

The volume or weight of the solution is adjusted to its desired value by adding sterile water. The solution is stirred at 40±5° C. during about 10 minutes then cooled to 15-30° C. under stirring. Samples of the solution are then collected for the usual control tests. The solution is subjected to aseptic filtration on a 0.2 μm membrane, then aseptically filled into 50 ml cylindrical vials to give 100 mg oxaliplatin per vial. Freeze-drying is performed using cycles of freezing, primary drying (sublimation) and secondary drying, according to techniques well known in the art. The vials containing the lyophilisate pharmaceutical formulation are stoppered and sealed.

EXAMPLE 5

Evaluation of the Relative Toxicity Due to the Presence of Oxalic Acid in Oxaliplatin Active Substance—Determination of Lethal Doses $LD_{10}$ Lethal doses $LD_{10}$ of a cytostatic active substance determinated in mice is generally considered as being a significative correlation with the maximum tolerated doses (MTD) in man.

Accordingly, a first group of CD-1 mice has received a solution of the oxaliplatin active substance as can be obtained in Example 1 and $LD_{10}$ is around 18.0 mg[[7]]/kg.

A second group of animals has received the same solution as for the first group, but with the addition of oxalic acid at a final concentration of 0.2 mM, and $LD_{10}$ is around 14.4.

Finally, a control group has only received a solution of oxalic acid at a concentration of 0.2 mM and no significant toxicity has been observed.

LD10 along with clinical symptoms demonstrate that the oxaliplatin active substance as can be obtained in Example 4, while administrated in solution, is less toxic as the same active substance, but administrated with oxalic acid.

The invention claimed is:
1. A pharmaceutical solution formulation comprising water and an oxaliplatin active substance, wherein the solution formulation has an oxalic acid content of 0.1 or 0.11 wt % relative to the oxaliplatin active substance.
2. A pharmaceutical formulation comprising a lyophilized oxaliplatin active substance, wherein the formulation has an oxalic acid content of 0.1 or 0.11 wt % relative to the oxaliplatin active substance.
3. The pharmaceutical solution formulation of claim 1, wherein the solution formulation has an oxalic acid content of 0.1 wt % relative to the oxaliplatin active substance.
4. The pharmaceutical formulation of claim 2, wherein the formulation has an oxalic acid content of 0.1 wt % relative to the oxaliplatin active substance.
5. The pharmaceutical solution formulation of claim 1, wherein the solution formulation has an oxalic acid content of 0.11 wt % relative to the oxaliplatin active substance.
6. The pharmaceutical formulation of claim 2, wherein the formulation has an oxalic acid content of 0.11 wt % relative to the oxaliplatin active substance.

* * * * *